United States Patent

Zauza

[11] Patent Number: 5,423,833
[45] Date of Patent: Jun. 13, 1995

[54] SURGICAL SUTURING INSTRUMENT

[75] Inventor: Konstantin Zauza, Baden, Austria

[73] Assignee: Ethicon Endo-Surgery, Cincinnati, Ohio

[21] Appl. No.: 143,006

[22] Filed: Oct. 26, 1993

[30] Foreign Application Priority Data

Nov. 24, 1992 [DE] Germany ............. 42 40 671.4
Jan. 29, 1993 [DE] Germany ............. 43 02 939.6

[51] Int. Cl.⁶ .............................................. A61B 17/04
[52] U.S. Cl. ................................... 606/139; 606/144; 606/148
[58] Field of Search ................... 606/139, 144–148

[56] References Cited

U.S. PATENT DOCUMENTS 2,614,564 10/1952 Giaccaglia et al. ............. 606/139
3,067,748 12/1962 Straith ............................ 606/139

FOREIGN PATENT DOCUMENTS 3203628 10/1982 Germany .
3136083 3/1983 Germany .

Primary Examiner—Stephen C. Pellegrino
Assistant Examiner—Gary Jackson
Attorney, Agent, or Firm—Paul A. Coletti

[57] ABSTRACT

A surgical suturing instrument has a first arm and a second arm which start with their proximal ends from a connection part and contain intermediate area attached to distal ends. A part of the intermediate area is occupied by a guide member which is designed and mounted in such a way that a suture thread introduced transversely in proximal direction into the intermediate area is guided by means of the guide member along the first arm limb until it has passed a guide point, and the thread, upon the return movement in distal direction, is guided by means of the guide member essentially along the second arm. The end of the surgical thread is secured to the guide member. The other end of the surgical thread is attached in the front zone of a surgical needle.

12 Claims, 4 Drawing Sheets

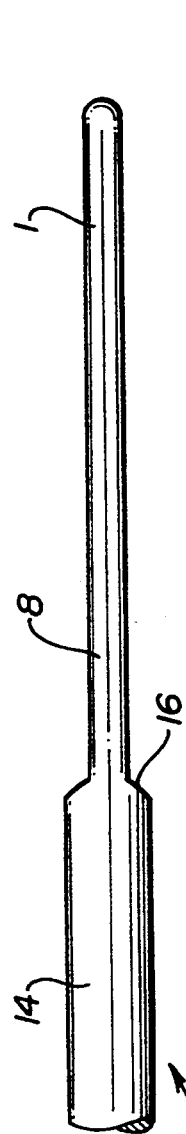
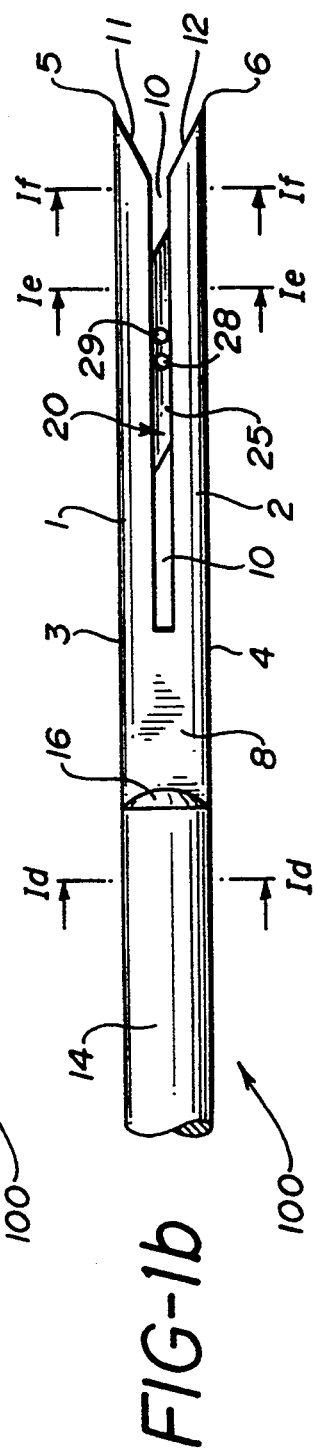
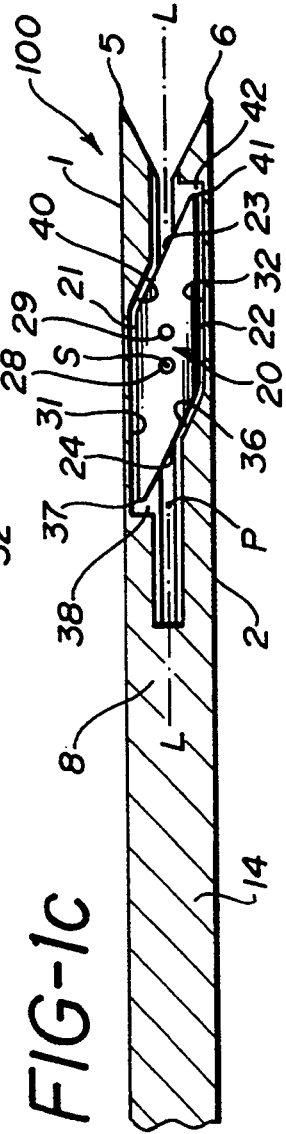
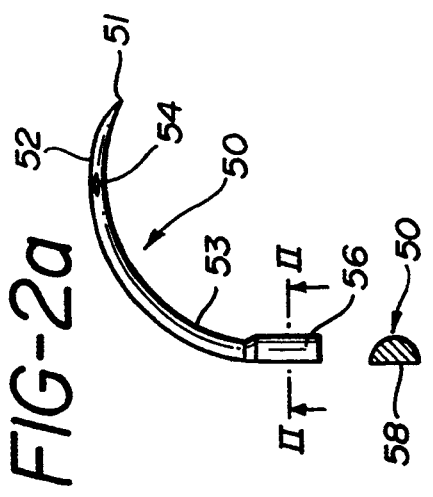

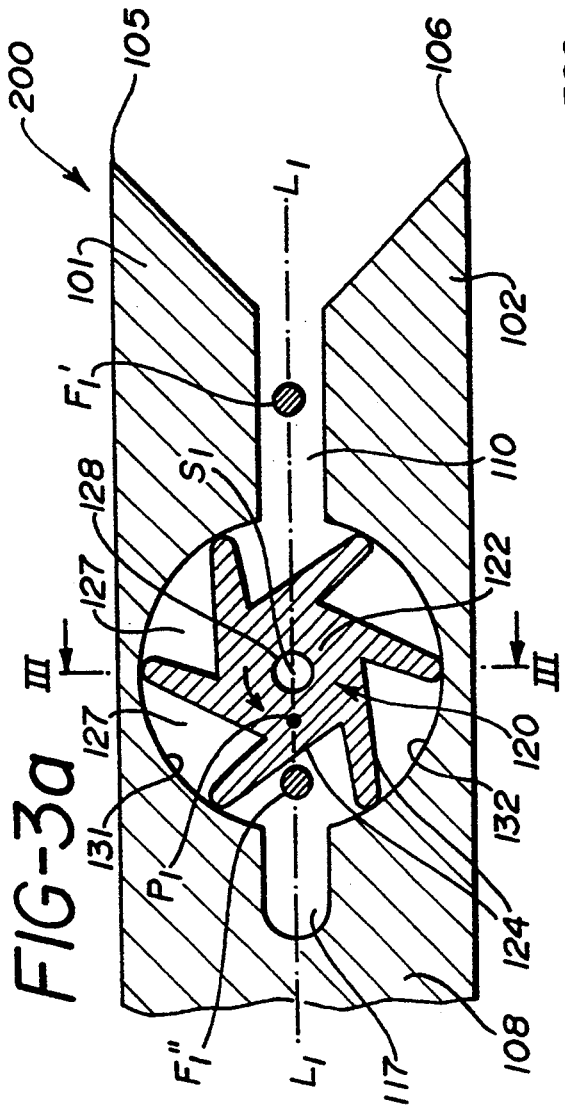
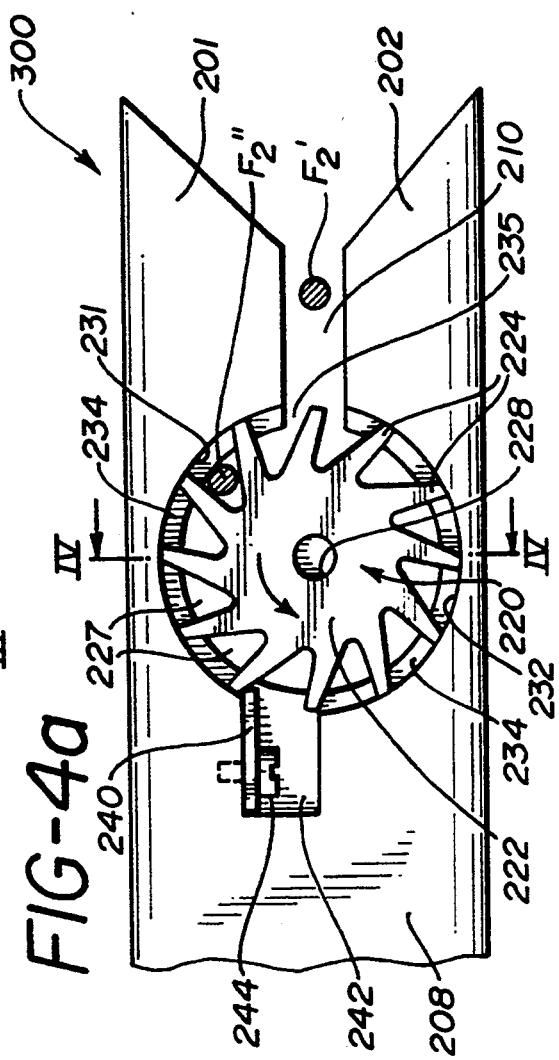
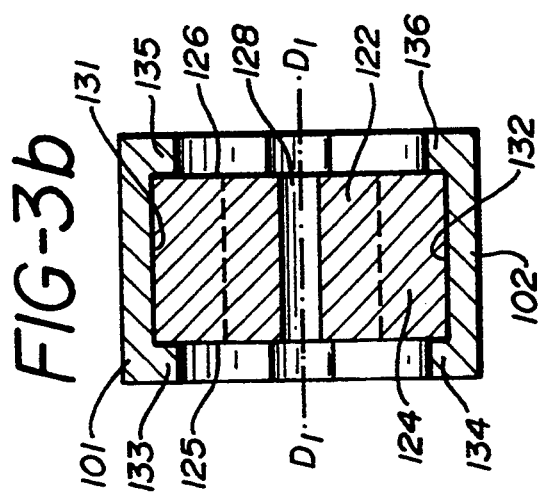
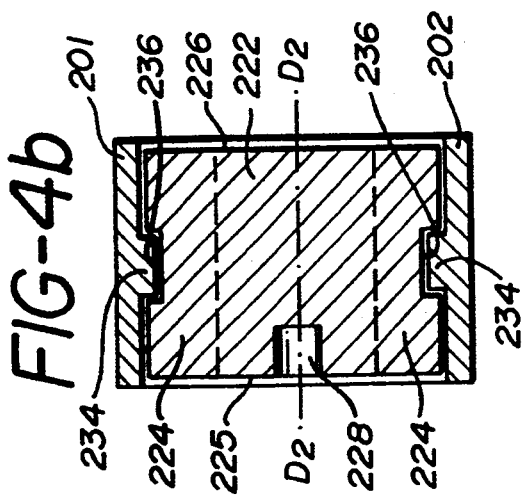

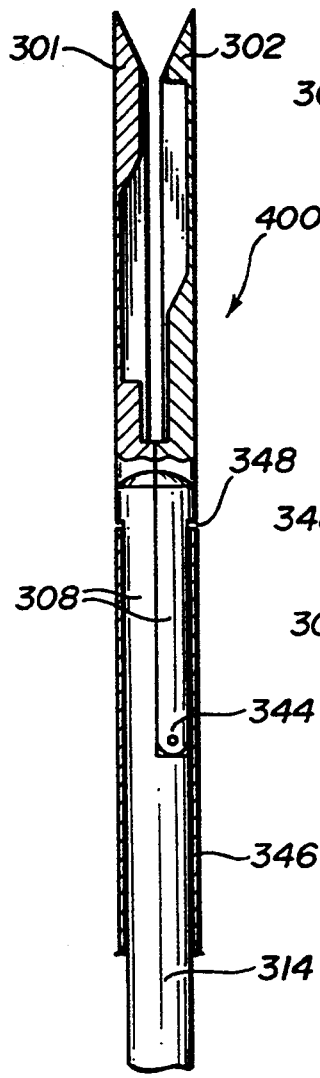
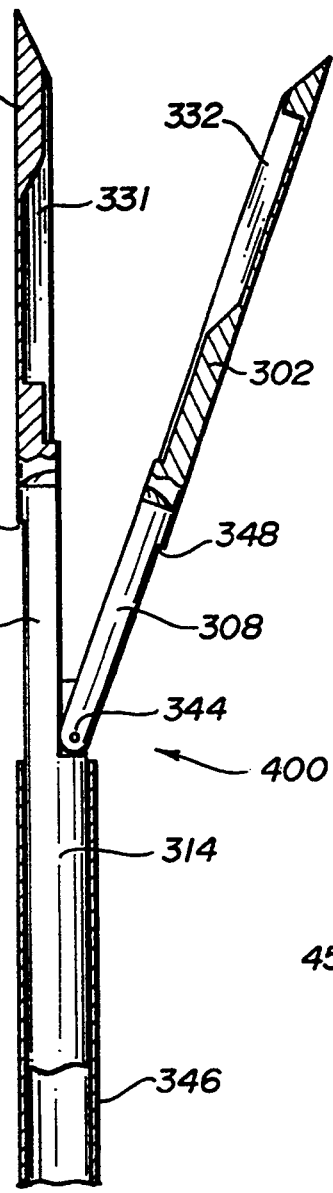
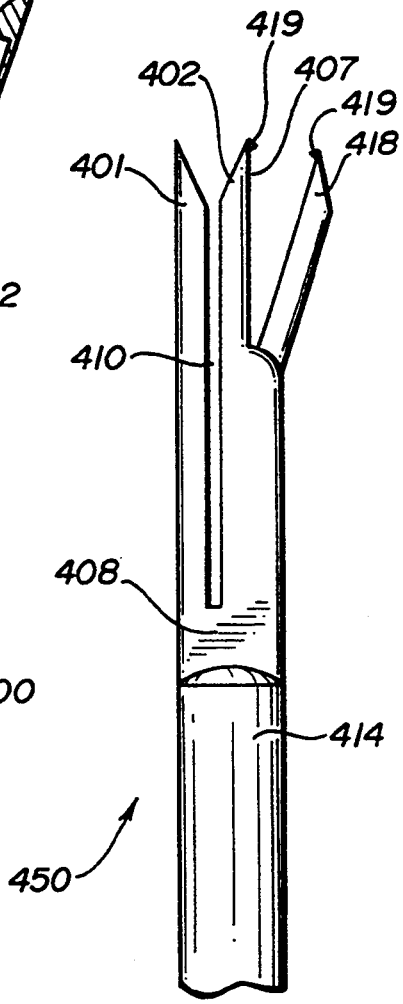
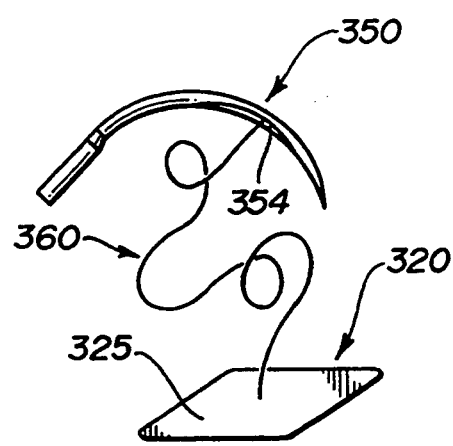

SURGICAL SUTURING INSTRUMENT

PRIORITY DATA

This application claims priority from DE P4240671.4, filed Nov. 24, 1992 and DE P4302939.6, filed Jan. 29, 1993, incorporated by reference.

BACKGROUND OF THE INVENTION

The invention relates to a surgical suturing instrument.

When surgical sutures are being laid, loops and knots must be formed. In an operative area which is difficult to access, this can be very difficult. This is true in particular for endoscopic operating techniques in which cannulae (trocar sleeves) must be inserted through the body wall, so as to make accessible the operative area, for example in the abdominal region. Observation equipment and operating instruments are introduced into the inside of the body through these cannulae. The creation of a suture from surgical suture material or the formation of a knot calls for very great skill from the operator if it is possible at all, as the mobility of the operating instruments is limited by the narrow cannulae. Also, the operator has only a two-dimensional impression of the operative field, which operative field is recorded via an endoscopic optical device and transmitted onto a television screen.

SUMMARY OF THE INVENTION

The object of the invention is to provide a surgical suturing instrument which greatly facilitates the formation of loops and knots in surgical suture material and in particular is also usable in endoscopic operations.

The surgical suturing instrument according to the invention has a first guide limb (arm) and a second guide limb (arm) which start with their proximal ends from a connection part and whose intermediate area is accessible from their distal ends. The two arms are preferably essentially straight and run parallel to each other, their front sides preferably being bevelled onto the intermediate area. A guide member which fills part of the intermediate area is held by one of the two arms or by both. The guide member is designed and mounted in a way so that a thread introduced transversely in the proximal direction into the intermediate area is inevitably guided essentially along the first arm by means of the guide member until it has passed a certain proximal point. Upon the return movement of the thread in the distal direction, the guide member inevitably guides it essentially along the second arm. The result of an easily performed to-and-fro movement of the surgical suturing instrument (much like a "sewing machine" needle) is thus that the thread extending transversely through the intermediate area, which thread portion is part of the suture material used, is guided round a point which lies between the two arms and on a side surface of the guide member. If the end of the thread is secured to the surgical suturing instrument in such a way that the thread starts from this point, a loop or knot may be formed in the thread. Thus the creation of the loop or knot does not require any complicated rotating and looping movements, but a to-and-fro movement which is simple to perform and easily controllable, even under endoscopic conditions.

In an advantageous version, the surgical suturing instrument is supplied with a surgical thread already secured to the guide member. The surgical needle attached to the other end of the surgical thread is preferably bent, and the thread-end is secured in its front zone, preferably in a groove arranged on the concave side of the surgical needle, which groove can also extend along a larger portion of the length of the needle towards the rear zone of the surgical needle. If the surgical suturing instrument according to the invention is provided with a surgical thread and a surgical needle designed in this way, a continuous suture can easily be created, as will be described in more detail in connection with the embodiments. The only instruments which have to be brought to the operative area through cannulae for this purpose are the surgical suturing instrument according to the invention with surgical thread and surgical needle, plus a conventional needle holder, which greatly facilitates the operation and also reduces the number of trocar punctures necessary to complete the operation. The surgical suturing instrument according to the invention may also be fitted with a gripper which can be operated, by means of an actuation part guided in longitudinally displaceable manner in the proximal end of the shaft of the surgical suturing instrument.

To introduce the surgical needle together with the surgical suturing instrument into the inside of the body without problems, it is advantageous if a securing device for the releasable holding of the surgical needle is provided in the region of the first and second arms or of the connection part. In a preferred version, the surgical needle held by the securing device is coverable by means of a protective sleeve which is displaceable by means of an actuation element guided in the shaft. Damage to the surgical needle and unintentional injuries to the patient are thus reliably avoided.

The connection part can be fitted on the shaft in a fixed or removable manner. The latter is particularly advantageous if the surgical suturing instrument according to the invention is designed as a partially re-usable product, in which the distal zone with the first and second arms, the connection part and the guide member, are discarded after the operation, while the shaft with actuation as well as the handle can be re-used after sterilization. Alternatively, the whole instrument can be designed as a disposable article or generally for re-use.

In an advantageous version of the surgical suturing instrument according to the invention, the guide member is removable. For this purpose, for example, the first arm could be rotatable relative to the second arm, and the two arms may be locked by a longitudinally displaceable sheath. Alternatively, one or both arms is designed to be detachable in order to permit access to the guide member. A design according to which the guide member is removable is advisable if the whole surgical suturing instrument except for the guide member is to be re-used after sterilization. Prepared suture material is suitable as a consumption article for use in such a surgical suturing instrument, which prepared suture material comprises a guide member matched to the surgical suturing instrument, a surgical thread secured with one end to the guide member and a bent surgical needle in the front zone of which the other end of the surgical thread is secured. The surgical needle and the surgical thread in terms of its thickness, its material and its structure (for example monofilaments or multifilaments) can be matched to the proposed operation.

Further, the guide member can be differently designed. It can be in the form of a parallelepiped whose longitudinal surfaces run essentially parallel to the first and second, the zone of the first longitudinal surface being loosely mounted in a groove of the first arm and the zone of the second longitudinal surface in a groove of the second arm so that a transversely running thread is movable through the intermediate space between the guide member and the inner surfaces of the groove in question. The distal end face of the guide member inclined with respect to the each respective arm, ensures that a thread introduced in proximal direction into the intermediate area is moved onto the first arm, while the proximal end face, also running inclined with respect to the first and second arms effects a sliding along the second arm upon the return movement. In this version the guide member has a particularly simple structure.

A guide member which essentially has the form of a wheel provided with at least one segment-like recess, which wheel is rotatably supported in a recess at the first arm and in a recess at the second arm, the axis of rotation leading through the intermediate area and essentially perpendicular to the longitudinal axis of the intermediate area, is suitable in particular for more vulnerable suture materials. The end of the surgical thread preferably runs through a bore in the zone of the axis of rotation of the wheel. In use, a thread introduced transversely in proximal direction into the intermediate area enters the segment-like recess first and then rotates the wheel, so that it moves once around its starting position at one side of the hub. The wheel is preferably designed with a series of segment-like recesses which adjoin one another in circumferential direction. A rotary movement in the undesired direction can be prevented by means of a stop pawl.

BRIEF DESCRIPTION OF THE DRAWINGS

The invention is explained in more detail below with the help of embodiments. The drawings show:

FIG. 1 a first version of the surgical suturing instrument according to the invention;; part 1(a) showing a plan view, part 1(b) a side view; part 1(c) a longitudinal section, the section plane being the central plane according to the representation in part 1(b); part 1(d) a cross-section along the line Id—Id from part 1(b); part 1(e) a cross-section along the line Ie—Ie from part (b); and part 1(f) a cross-section along the line If—If from part 1(b);

FIG. 2 a surgical needle used with the surgical suturing instrument; part 2(a) showing a side view; and part 2(b) a cross-section along the line II—II from part 2(a);

FIG. 3 a second version of the surgical suturing instrument according to the invention, part 3(a) showing a longitudinal section in the central plane; and part 3(b) a cross-section along the line III—III from part 3(a);

FIG. 4 a third version of the surgical suturing instrument according to the invention, part 4(a) showing a side view; and part 4(b) a cross-section along the line IV—IV from part 4(a);

FIG. 5 another version of the surgical suturing instrument according to the invention which largely corresponds to that represented in FIG. 1, but in which the guide member is removable; part 5(a) showing a longitudinal section with the guide limbs in the operating position; and part 5(b) a longitudinal section with the guide limbs rotated for the removal of the guide member;

FIG. 6 a view of prepared suture material with a surgical needle, a surgical thread and a guide member for use with the surgical suturing instrument represented in FIG. 5;

FIG. 7 a side view of a version of the surgical suturing instrument according to the invention, provided with an additional rotatable gripping law;

DETAILED DESCRIPTION OF THE INVENTION

Figure 8:
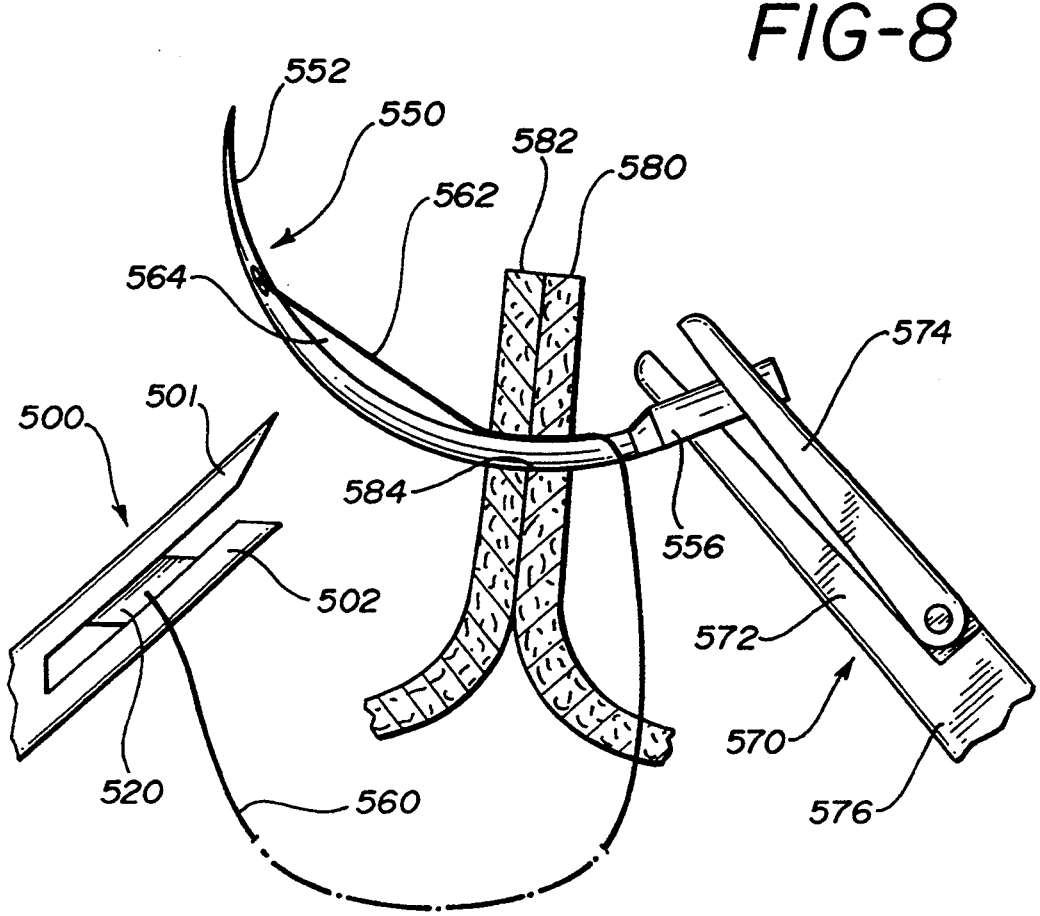
FIG. 8 a diagrammatic representation of the application of the surgical suturing instrument according to the invention.

FIG. 1 shows a first embodiment of the surgical suturing instrument 100 according to the invention. A first arm, designed essentially straight and rod-shaped, with a proximal end 3 and a distal end 5, runs parallel to a correspondingly designed second arm 2 with a proximal end 4 and a distal end 6. The first arm limb 1 and the second arm limb 2 start with their respective proximal ends 3, 4 from a connection part 8. Formed between the two guide limbs 1 and 2 is the slit-shaped intermediate area 10 which is accessible from the distal ends 5 and 6 of arms 1 and 2 and from the side. The front side 11 of the first arm 1 and the front side 12 of the second arm 2 are bevelled onto the intermediate area 10.

Joined to the proximal end of the connection part 8 is a shaft 14 which is designed integral with the connection part 8 in the embodiment. A rounded transitional zone 16 between the shaft 14, round in cross-section, compare FIG. 1(d), and the flat-shaped connection part 8 (compare FIGS. 1(a) and 1(f)), avoids sharp-edged transitions. In an alternative version, the connection part 8 can be fitted on the shaft 14 via a releasable coupling.

As can be seen in particular from FIGS. 1(c) and 1(e), part of the intermediate area 10 is occupied by a guide member 20. The guide member 20 is located in the middle zone of the intermediate area 10, so that a distal and a proximal zone remain free. The form of the guide member 20 is essentially that of a parallelepiped with a first longitudinal surface 21, a second longitudinal surface 22, a distal end surface 23, a proximal end surface 24, a side surface 25 and a side surface 26. The edges of the guide member 20 are preferably rounded. Through-holes 28 and 29 are arranged in the middle section of the side surfaces 25 and 26.

The guide member 20 is housed in a groove 31 with which the first arm 1 is provided, and in a corresponding groove 32 of the second arm 2. The first longitudinal surface 21 and the second longitudinal surface 22 run parallel to the first arm 1 and to the second arm 2. The holes 28 and 29 lie on the longitudinal axis L—L of the intermediate area 10. There is some "play" between the guide member 20 and the inner surfaces of groove 31 and groove 32, so that a suture thread F inserted transversely into the intermediate area 10 can be moved over the guide member 20, see FIG. 1(e). When the thread F is moved in proximal direction, it is guided along the guide member 20 until a part of the obliquely lying end surface 24 abuts against a projecting surface 36 which forms an end of the groove 32. There still remains, at the proximal end 37 of the guide member 20, a gap 38 through which the thread F can pass. If the thread F is now moved back in the distal direction, the guide member 20 shifts slightly in the same direction until the upper zone of the distal end surface 23 abuts against a projecting surface 40; a gap 42 then remaining at the distal end 41 of the guide member 20 is sufficient for the passage of the transversely running thread F.

Thus, if thread F enters the intermediate area 10 essentially across or transversely from the distal ends 5 and 6 and is then moved in the proximal direction relative to the surgical suturing instrument, it glides along the inclined distal end surface 23 of the guide member 20 and thus inevitably onto the first arm 1. It is then guided in the groove 31 essentially along the first guide limb 1. As soon as the proximal end 37 of the guide member 20 is reached, which, seen in longitudinal direction, corresponds to a guide point P on the longitudinal axis L—L of the intermediate area 10, the thread F slides along the inclined proximal end surface 24 upon the return movement in the distal direction, enters the groove 32 and finally leaves the surgical instrument between the distal ends 5 and 6 of the arms, respectively. In this way the thread F is inevitably guided once around point S, which coincides with the hole 28.

At point S, the surgical thread used during the operation starts from the guide member 20 (not shown in FIG. 1). The end of the surgical thread F is preferably secured to the guide member 20, for example by passing the end portion of the surgical thread through the hole 28 (point S) and then through the hole 29 and securing it there with a drop of tissue or suture adhesive. With the described rotational movement, in which the front portion of the surgical thread is guided transversely around the guide member 20 and thus point S, a loop is formed in the surgical thread F.

In a version which is modified compared with FIG. 1, the guide member is somewhat differently shaped, its longitudinal section in the section plane according to FIG. 1(c) being essentially in the form of a parallelogram, as in FIG. 1(c), while its cross-section is more markedly rounded, e.g. its cross-section is circular.

FIG. 2 shows a surgical needle 50 with a tip 51 which is attached to the other end of the surgical thread. The surgical needle 50 is preferably curved, which greatly facilitates the insertion of the suture into tissue. The surgical thread F is secured in the front zone 52, preferably in a groove 54 arranged on the concave side 53. The rear zone 56 of the surgical needle 50 is preferably provided with a flat area 58, see FIG. 2(b). As a result, the surgical needle 50 cannot rotate when it is gripped with a needle holder.

In the embodiment represented in FIG. 2(a), the groove 54 arranged on the concave side 53 of the surgical needle 50 is relatively short and therefore extends only in a zone close to the tip 51. In an alternative version, groove 54 runs along a larger portion of the length of the needle, preferably up to the rear zone 56. This provides the advantage that the tissue hole (made by penetration of the surgical needle 50 including the surgical thread) will not be too large. In this case, the thread F enters the groove extending on the concave side 53 during the penetration of the tissue, resulting in a smaller hole is the tissue. A similarly positive effect is also achieved when the cross section of the needle is designed to have a flat section on the concave side 53, in a zone from the securing position of the surgical thread F preferably extending to near rear zone 56. In this case the common contour of the needle and the thread F is essentially circular, which is advantageous for the tissue being penetrated.

In the version represented in FIG. 1, the guide member 20 is not removable. The surgical suturing instrument 100 according to this embodiment is preferably designed as a disposable article and comprises the parts shown in FIG. 1 (to which is also added a handle at the proximal end of the shaft 14), a surgical thread F secured with one end at the guide member 20, and a surgical needle 50 which is preferably designed according to FIG. 2. Alternatively, a new surgical thread F could be secured to the guide member 20 before every use.

In the embodiment 200 represented in FIG. 3, the guide member is in the form of a wheel. The remaining structure of the surgical instrument is similar to that of the version according to FIG. 1. A first arm 101 with a distal end 105 and a second arm 102 with a distal end 106 run essentially parallel to each other and are connected to each other via a connection part 108 which is only roughly outlined in FIG. 3. The intermediate area 110 comprises (just as in the first embodiment) a proximal zone 117. The guide member 120 is in the form of a wheel with outwardly extending partitions 124 starting from a hub 122 and containing side surfaces 125 and 126. The recesses 127 formed in this way between the partitions 124 are segment-like but differ from an exact segment shape, as can be seen from FIG. 3(a). A bore 128 runs through the centre of the hub 122.

The guide member 120 is rotatably supported in a recess 131 provided in the first arm 101 and in a corresponding recess 132 of the second arm 102. Lateral projections 133 and 135 at the first guide limb 101, which enclose the lateral edges of the recess 131, and corresponding lateral projections 134 and 136 formed at the second arm 102 prevent a lateral dropping-out of the guide member 120, see FIG. 3(b). The axis of rotation is designated $D_1$—$D_1$.

If a thread $F_1'$ which is running essentially transversely, enters the intermediate area 110 and is moved in proximal direction, it first runs essentially along the longitudinal axis $L_1$—$L_1$ of intermediate area 110. When thread $F_1'$ reaches the region of a recess 127 of the guide member 120, it can initially exert no noteworthy torque on the guide member 120, as the axis of rotation $D_1$—$D_1$ intersects the longitudinal axis $L_1$—$L_1$ of the intermediate area 110. At the inclined partition 124 it glides upwards, i.e. onto the first guide limb 101. Now the torque is large enough to effect a rotary movement of the guide member 120 (in the direction of the arrow) upon further movement of the thread in proximal direction. If the thread has reached the position designated $F_1''$ in FIG. 3(a), it has passed the guide point $P_1$. Upon return movement of the thread, it is guided essentially along the second guide limb 102, until the guide member 120 has completed a rotatory movement of some 360° and the thread can again leave the intermediate area 110. The thread is thus inevitably guided once round the point $S_1$ which coincides with the bore 128.

The end of the surgical thread is secured in the bore 128, for example using a tissue adhesive glue. If the surgical thread is sensitive to twisting, as friction-free as possible a guidance of the thread-end through the bore 128 is recommended without the thread being firmly connected to the hub 122, so that it does not participate in the rotary movement of the guide member 120. This can be managed for example through a bore whose internal diameter is clearly greater than the diameter of the surgical thread; the surgical thread could be secured against dropping out by an end-knot. Another rotatable mounting results if the thread-end is clamped or glued in a sheath which can be engaged in the bore 128 and thereafter still allows a relative movement with respect to the hub 122.

The surgical suturing instrument represented in FIG. 3 is suitable in particular for sensitive suture thread material, as the surgical thread does not have to be passed through a relatively narrow intermediate space as in the first embodiment, compare in particular FIG. 1(e).

The embodiment 300 shown in FIG. 4 is largely the same as that represented in FIG. 3. A first arm 201 and a second arm 202 are connected to each other via a connection part 208. The intermediate area 210 has only a distal zone. The guide member 220 is again designed like a paddle wheel and has a hub 222 with side surfaces 225 and 226 as well as partitions 224 which delimit individual segment-like recesses 227 from each other.

The guide member 220 is rotatably mounted in a largely segment-shaped recess 231 in the first arm 201 and in a corresponding recess 232 in the second arm 202. A lateral dropping-out of the suture material is prevented by a rib-shaped projection 234 which engages in corresponding recesses 236 in the partitions 224, see FIG. 4(b). Projection 234 extends virtually round the whole periphery of the guide member 220; only in the distal zone does there remain a gap 235 which has the same width as intermediate area 210. A thread ($F_2'$, $F_2''$) which is introduced transversely via intermediate area 210 into guide member 220 therefore cannot leave the region of the guide member 220 while it is guided through the instrument.

An inevitable rotary movement in the direction of the arrow is again achieved through the configuration and inclined position of the partitions 224. Additionally, a stop pawl 240 which is secured in a recess 242 on one side of the connection part 208 by a screw 244 prevents the guide member 220 from being inadvertently rotated in the wrong direction.

A blind hole 228 in the region of the axis of rotation $D_2$—$D_2$ on the side surface 225 serves to secure the end of a surgical thread.

With the versions described thus far of the surgical suturing instrument according to the invention, the guide member is not removable. These versions are accordingly suitable as disposable articles. Alternatively, a fresh surgical thread may be secured to the guide member after every application. In the embodiment 400 represented in FIG. 5, on the other hand, the two guide limbs can be unfolded from each other for the insertion or removal of the guide member.

The version shown in FIG. 5 otherwise agrees largely with that according to FIG. 1. A first arm 301 and a second arm 302 are connected to each other via a connection part 308. The connection part 308 itself is divided in two parts, the part forming the extension of the second arm 302 being rotatably pivoted at its proximal end via a hinge 344 at a shaft 314. The other part of the connection part 308 is connected in one piece with the shaft 314. In order to lock the two arms 301 and 302 relative to each other for the use of the surgical suturing instrument, a sheath 346 is provided which encloses the distal zone of the shaft 314 and is longitudinally displaceable. When it is pushed forward in distal direction its distal end abuts against an annular projecting surface 348, and the two guide limbs 301 and 302 are locked relative to each other, see FIG. 5(a). To swivel the two arms 301 and 302 away from each other, the sheath 346 must be pushed in proximal direction, see FIG. 5(b). Now a guide member is the form of a parallelepiped (not shown in FIG. 5) can be inserted into a groove 331 at the first arm 301 and a groove 332 in the second arm 302. An unintentional displacement of the sheath 346 can be prevented by friction or by a conformable stop device not shown in FIG. 5.

FIG. 6 shows prepared suture material cartridge for use in the surgical suturing instrument 400 represented in FIG. 5. The prepared suture material comprises a guide member 320, to one side surface 325 of which one end of a surgical thread 360 is secured. The other end of the surgical thread 360 is attached in a groove 354 in the front zone of a surgical needle 350. The prepared suture material is suitable as a disposable article for a reusable surgical suturing instrument according to FIG. 5. Other versions, for example with a differently designed guide member which must be matched to their surgical suturing instrument used, are also conceivable. Moreover, the groove 354 could extend along a larger portion of the concave side of the surgical needle 350 so that during penetration of the tissue the surgical thread 360 can lie in the groove 354, as explained with regard to FIG. 2.

In order to enable insertion or removal of the guide member other designs of the surgical suturing instrument are possible according to which designs the guide member becomes accessible in a way which is different from that described before. For example, the first arm or the second arm (or both) could be designed to be detachable from the surgical suturing instrument. For this purpose, for example, at the proximal end of the guide limb in question there could be provided a pin being insertible into a corresponding opening at the connection part and being lockable there. Many other design possibilities are conceivable.

FIG. 7 shows another version of the surgical suturing instrument 450 according to the invention. A first arm 401 and a second arm 402 are mounted on a shaft 414 via a connection part 408. The distal zone of the external side 407, pointing away from the intermediate area 410, of the second arm 402 is designed as a fixed gripping jaw with a claw 419. A movable gripping jaw 418 with a corresponding claw 419 is rotatable against this fixed gripping jaw. Housed longitudinally displaceable, in a manner familiar to the person skilled in the art, in the inner space of the hollow shaft 414 and of the hollow proximal zone of the second arm 402 is an essentially rod-shaped actuation part (not shown in FIG. 7). The actuation part can be displaced via the handle (not shown in FIG. 7) at the proximal end of the shaft 414, which effects a swivel movement of the gripping jaw 418.

During endoscopic operations, the gripper alongside the guide limbs is of major advantage. If the surgical suturing instrument is used to form a loop or a knot, as is described below, the gripper is not needed. To prepare such a suturing step, however, the surgical needle must be pushed with the help of a separate needle holder through two tissue edges which are to be connected to each other. During this process, the two tissue edges should be fixed relative to each other. This can be done by using a gripping instrument introduced additionally through a cannula or by using the gripper attached to the surgical suturing instrument. This gripper thus saves the use of an additional operation instrument. The progress of the operation procedure thereby becomes easier to supervise, fewer coordination problems occur and, where appropriate, the use of an additional cannula can be avoided.

In order to guide the surgical suturing instrument according to the invention through a cannula to the operative field without problems during endoscopic operations, it can be advantageous if the surgical needle used is secured in the distal zone of the surgical suturing instrument during this process. To this end, a securing means for the releasable holding of the surgical needle can be provided in the region of the guide limbs or of the connection part. In order to avoid injury to the patient or damage to the needle, the needle is preferably covered by a protective sleeve. This protective sleeve can be so designed that it can be moved away in a manner familiar to the person skilled in the art by means of an actuation element guided in the shaft of the surgical suturing instrument and operated from the handle, so that the needle is exposed thereafter and can be removed with the help of a separate needle holder.

FIG. 8 is a diagrammatic representation which shows the application of the surgical suturing instrument 500 according to the invention for the setting of a continuous suture. In principle, the surgical suturing instrument can also be used in open surgery; however, it proves particularly advantageous in endoscopic applications, wherein the operative area is difficult of access. The following description thus applies to an endoscopic operation.

At the beginning, the surgical suturing instrument 500 according to the invention with the first arm 501 and the second arm 502 and as well as the guide member 520, the surgical needle 550 and the surgical thread 560 is introduced into the inside of the body through a cannula via a shaft which is not shown in FIG. 8. The aim is to connect to each other a first tissue edge 580 and a second tissue edge 582, which are turned against each other, by means of a continuous suture. Such a continuous suture is represented in plan view in FIG. 9. The surgical needle 550 is initially gripped in its rear zone 556 by a conventional endoscopic needle holder 570 which has a fixed gripping jaw 572, a rotatable gripping jaw 574 and a shaft 576. It is then pushed through the two tissue edges 580 and 582 at a puncture point 584 (see also FIG. 9). To this end, the tissue edges 580 and 582 must be fixed, for example with the help of a gripper attached to the surgical suturing instrument or with the help of an additionally introduced gripping instrument. Once the surgical needle 550 is sticking in the tissue edges 580 and 582, it holds them together and an additional fixing is not necessary.

As the surgical thread 560 is secured in the front zone 552 of the bent surgical needle 550 and it is pressed against the surgical needle 550 by the tissue at the puncture point 584, the front portion of thread 562 is stretched, which produces an intermediate space 564 between the front portion of thread 562 and the surgical needle 550. In order to form a loop 590 in the surgical thread 560 at the puncture point 584, the surgical suturing instrument 500 is moved to the surgical needle 550, as represented in FIG. 8. The second arm 502 penetrates the intermediate space 564, a step facilitated by the bevelled front side of the second arm 502. Upon further forward movement of the surgical suturing instrument 500, the front portion of thread 562 running transversely between the two guide limbs 501 and 502 is moved against the first guide limb 501 by the guide member 520. If the guide point is passed, as described above, the surgical suturing instrument 500 is pulled back, so that the front portion of thread 562 is moved in distal direction relative to the surgical suturing instrument 500. In this way, the front portion of thread 562 is guided once round the rear end of the surgical thread 560, whereupon a loop 590 with the shape shown in FIG. 9 results.

The operator then pulls the surgical needle 550 back out of the puncture point 584 with the help of the needle holder 570. He must now ensure that a sufficiently long portion of the surgical thread 560 is present both on the side of the first tissue edge 580, where the surgical needle 550 is located, and on the side of the second tissue edge 582, where the surgical suturing instrument 500 is, and can achieve this by further pulling on the surgical needle 550. As the next step, the needle is applied at the puncture point 585 and the described process is repeated, which results in loop 591. This procedure is continued until the suture has reached the desired length.

Figure 9:
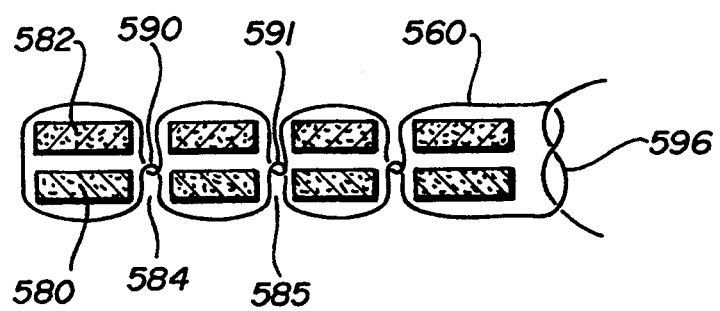
FIG. 9 a diagrammatic representation of a continuous suture produced according to FIG. 8 with an end-knot.

To form at the end a knot 596 of the shape shown in FIG. 9, the thread-end allocated to the surgical needle 550 is stretched with the help of the needle holder 570. The surgical suturing instrument 500 is then rotated by 180° about its longitudinal axis, so that the second guide limb 502 now comes to rest on top and the first guide limb 501 underneath. As the surgical thread 560 is flexible, the surgical thread 560 can be prevented from coiling about the surgical suturing instrument 500 during this half rotation. If a forward-and-back movement of the surgical instrument 500 is now carried out relative to the transversely running stretched thread-end, a single knot 596 with the form represented in FIG. 9 results. It can then be pulled tight.

The surgical suturing instrument according to the invention also allows knots with other forms to be created. For example, the surgical thread 560 can be wound once or several times round the surgical suturing instrument 500 in the region of its end starting from the guide member 520, in the proximal zone of the two arms 501, 502 or in the region of the connection part. This can be achieved, for example, through a rotary movement of the surgical suturing instrument 500 about its longitudinal axis. The surgical suturing instrument 500 is then moved forwards and backwards in relation to the transversely stretched other end of the surgical thread 560. A particularly secure knot can be achieved if the end portion (starting from the surgical suturing instrument 500), of the thread is afterwards wound in the opposite direction round the surgical suturing instrument 500, after which the surgical suturing instrument 500 must once again be moved forwards and backwards in relation to the transversely running other thread-end.

It is clear from this description that the surgical suturing instrument according to the invention has a wide field of application and can be used, not only for the creation of continuous sutures in which one end of the surgical thread is knotted with the other end, but also for the formation of single-knot sutures in which the surgical thread is knotted after every stitch. Threads of any desired strength, made from any desired material suitable for medical purposes or of different structures (monofilament and multifilament threads) can be used.

Of course, even if a curved surgical needle is not used, the surgical suturing instrument according to the invention can be applied to advantage, in particular for knotting.

In principle, the surgical thread 560 used should not be too long, in order that undesirable entanglements do not result in the operative field. If a continuous suture is being created, the thread must also be pulled back and tightened with the surgical needle after every stitch. As there is not a large range of movement available for the surgical needle during endoscopic operations, suturing is substantially facilitated by a short surgical thread matched to the desired suture length.

I claim:

1. Surgical suturing instrument comprising:

a length of suture;

a first arm and a second arm connected at their proximal ends and each containing an intermediate area and distal ends;

a guide member mounted on one of said arms, said guide member comprising a part of a said intermediate area on the arm on which said guide member is contained, said guide member being configured in such a way that said suture is guided by said guide member along the arm containing said guide member until said suture has passed a predetermined guide point of said intermediate area along said arm containing said guide member, and further that the suture may be guided by means of said guide member along the other of said arms;

one end of said suture being securable to said surgical suturing instrument at a proximal end of said suture; and wherein said sutured is secured to said guide member, so that the suture lies on said guide member between said first arm and said second arm.

2. Surgical suturing instrument according to claim 1 further comprising a surgical needle secured at a distal end of said suture.

3. Surgical suturing instrument according to claim 1 wherein the first arm and the second arm are parallel to one another.

4. Surgical suturing instrument according to claim 3 wherein the guide member is shaped as a parallelepiped containing first and second longitudinal surfaces which run essentially parallel to said arms, a first longitudinal surface being mounted to said first arm and a second longitudinal surface mountable to said second arm so that said suture is movable through said guide member and said arms; and said guide member further containing a pair of surfaces connecting said longitudinal surfaces.

5. Surgical suturing instrument according to claim 3 wherein the guide member comprises a wheel provided with at least one segment-like recess, wherein the wheel is rotatably supported by said first arm and said second arm, the axis of rotation of said wheel running through the intermediate area of said arms.

6. Surgical suturing instrument according to claim 5 wherein said wheel contains a series of segment-like recesses which adjoin one another at the center of said wheel.

7. Surgical suturing instrument according to claim 1 wherein alongside one of said arms, a gripper is arranged which is actuable by means of an actuation part guided within a shaft connected to said arms and extending proximally therefrom.

8. Surgical suturing instrument according to claim 1 wherein said guide member is removable from said arms.

9. Surgical suturing instrument according to claim 1 wherein the first arm is rotatable relative to the second arm.

10. Surgical suturing instrument according to claim 1 wherein the guide member comprises a rotatably supported by said first arm and said second arm, the axis of rotation of said wheel running through the intermediate area of said arms.

11. Surgical suturing instrument according to claim 10 wherein said wheel contains a series of segment-like recesses which adjoin one another at the center of said wheel.

12. Surgical suturing instrument according to claim 10 wherein said guide member is removable from said arms.

* * * * *